United States Patent [19]
Animati et al.

[11] Patent Number: 5,670,534
[45] Date of Patent: Sep. 23, 1997

[54] DISTAMYCIN A DERIVATIVES AS ANTI-MALARIAL AGENTS

[75] Inventors: Fabio Animati, Rome; Federico Arcamone, Nerviano; Paolo Lombardi, Cesate; Cristina Rossi, Rome, all of Italy

[73] Assignees: A. Menarini Industrie Farmaceutice Reunite S.R.L.; Bristol Myers Squibb S.P.A., both of Italy

[21] Appl. No.: 549,737
[22] PCT Filed: Apr. 21, 1994
[86] PCT No.: PCT/EP94/01235
§ 371 Date: Feb. 16, 1996
§ 102(e) Date: Feb. 16, 1996
[87] PCT Pub. No.: WO94/25436
PCT Pub. Date: Nov. 10, 1994

[30] Foreign Application Priority Data
Apr. 26, 1993 [IT] Italy ................ FI93A0083

[51] Int. Cl.$^6$ .............. A61K 31/40; C07D 403/14
[52] U.S. Cl. ................................. 514/422; 548/518
[58] Field of Search ........................... 514/422; 548/518

[56] References Cited

FOREIGN PATENT DOCUMENTS

| | | |
|---|---|---|
| 9209574 | 11/1992 | European Pat. Off. . |
| 9313739 | 3/1993 | European Pat. Off. . |

OTHER PUBLICATIONS

Gendler et al. J. of Medicinal Chem., 24, 33–38 (1980).

*Primary Examiner*—Joseph McKane
*Attorney, Agent, or Firm*—Abelman, Frayne & Schwab

[57] ABSTRACT

The present invention relates to Distamycin compounds of formula (I), methods of use and their pharmaceutical compositions.

7 Claims, No Drawings

DISTAMYCIN A DERIVATIVES AS ANTI-MALARIAL AGENTS

This application is a 371 of PCT/EP94/01235 filed Apr. 21, 1994.

FIELD OF THE INVENTION

The present invention refers to pyrrol-amidinic compounds of general formula (I)

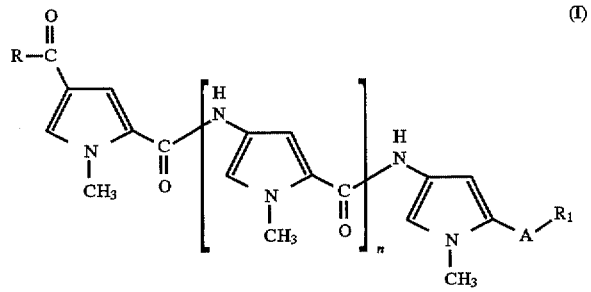

and their pharmaceutically acceptable salts wherein:

n is 0 or an integer comprised between 1 and 4;

R is chosen in the group consisting of H, $-OR_2$, $-NR_3R_4$ wherein:

$R_2$ is chosen in the group consisting of H, $C_{1-4}$alkyl, cycloalkyl, arylalkyl, aromatic residue;

$R_3$ and $R_4$, same or different, are chosen in the group consisting of:

H, alkyl, cycloalkyl, aromatic-residue, arylalkylyc-residue, arylalchyl- or eterocycle-residue possibly substituted with a formamido- or carbamoyle-group or $R_3$ and $R_4$, joined together, form an alkylene-residue or a group $-(CH_2)_2-O-(CH_2)_2$ or a group $-(CH_2)_2-NH-(CH_2)_2-$;

A is chosen in the group consisting of: simple chemical bond, the group $-CO-NH-Z$ wherein Z is chosen in the group consisting of an alkylene residue, aromatic residue;

$R_1$ is chosen in the group consisting of: $COOR_5$, $-B-NR_6R_7$,

an heterocyclic residue containing nitrogen wherein:

$R_5$ is chosen in the group consisting of H, alkyl, cycloalkyl, aromatic ring, arylalkyl, steroid-residue;

B is chosen in the group consisting of: simple chemical bond, C=O;

$R_6$ and $R_7$, same or different, are chosen in the group consisting of:

H, alkyl, cycloalkyl, aromatic group, arylalkyl, or $R_6$ and $R_7$ joined together form an alkylene-group, a group $-(CH_2)_2-O-(CH_2)_2-$ or a group $-(CH_2)_2-NH-(CH_2)_2-$ with the proviso that:

when $R_1$ is $-B-NR_6R_7$ and B is a simple chemical bond A is not a simple chemical bond;

when $R_1$ is an eterocyle-residue A is not a simple chemical bond when R is $NH_2$, A is the group $CO-NH-Z$, wherein Z is $-CH_2-CH_2$ and $R_1$ is

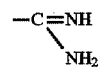

then n is different from 1;

when R is the group $NH_2$, $R_1$ is $-COOH$ and A is a simple chemical bond, then n is different from 0;

when R is OH, $R_1$ is

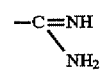

and A is the group $-CO-NH-Z$, than Z is different from $-CH_2-CH_2$.

STATE OF THE ART

Malaria is one of the most important diseases transmitted by arthropods largely diffused in tropical and also temperate zones either endemically or epidemically.

The world population living in malaric areas is more then 40%. The Health World Organisation calculates that there are 210–220 millions cases of infection per year, 85% of which caused by the parasite *Plasmodium falciparum*, with more than one million of casualties.

These records, joined with the drawback of *Plasmodi falciparum* strains resistent to the most common pharmaceticals in use, for example chloroquine, makes it necessary the development of new anti-malaric agents.

DETAILED DESCRIPTION OF THE INVENTION

The present invention provides new antiparasitic compounds, particularly structurally related to the antibiotic Dystamicine A (II), characterized by the presence of a carboxylic group, suitably derivatized, replacing the N-terminal chain in the naturally occurring product, and, possibly, further characterized by the introduction of chemical modifications in the C-terminal chain and by a different number of pyrrole-rings.

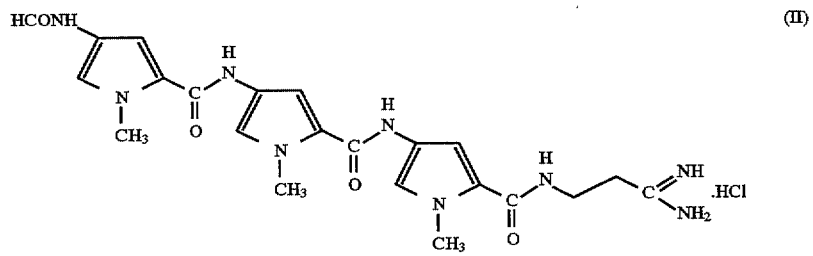

These compounds present an high antiparasitic activity, particularly with respect to protozoa as for example plasmodia which are responsible of the desease, trypanosomes, which are responsible of various trypanosomiasis, and protozoa belonging to the genus Leishmania which are responsible of leishmaniasis and also with respect to *Toxoplasma gondii, Pneumocystis carinii* and *Criptosporidum parvum*, this latter being the agents of serious infections especially in immunodepressed patients as for example patients affected by AIDS.

Furthermore the compounds according to the invection present an antiviral action.

The compounds according to the invention are compounds of formula (I) as previously defined.

Among the compounds of formula (I) as above defined preferred are those wherein:

n is as above defined;

R is: H;

$OR_2$, wherein $R_2$ is chosen in the group consisting of H, $C_{1-6}$ alkyl, $C_{3-7}$cycloalkyl, aryl$C_{1-4}$alkyl;

—$NR_3R_4$ wherein $R_3$ and $R_4$, independently from each other, are chosen in the group consisting of H, $C_{1-6}$alkyl, $C_{3-7}$cycloalkyl, phenyl, aryl$C_{1-4}$alkyl, heterocycle-residue containing one or more O, N, S atoms possibly substituted with a formamido or carbamoyl-group or, taken together, $R_3$ and $R_4$ form an $C_{3-4}$alkylene-residue, —$(CH_2)_2$—O—$(CH_2)_2$—, —$(CH_2)_2$—NH—$(CH_2)_2$—;

A is a simple chemical bond, the group —CO—NH—Z wherein Z is a $C_{2-6}$alkylene-residue, o-phenylene, p-phenylene, m-phenylene;

$R_1$ is chosen in the group consisting of:

$COOR_5$, wherein $R_5$ is H, $C_{1-6}$alkyl, $C_{3-7}$cycloalkyl, aryl$C_{1-4}$alkyl, phenyl, steroid-residue;

—B—$NR_6R_7$ wherein B is a simple chemical bond or CO and $R_6$ and $R_7$, independently from each other, are H, $C_{1-6}$alkyl, $C_{3-7}$cycloalkyl, aryl$C_{1-4}$alkyl; or taken together form a $C_{3-4}$alkyl residue, —$(CH_2)_2$—O—$(CH_2)_2$—, —$(CH_2)_2$—NH—$(CH_2)_2$;

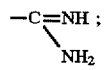

an heterocyclic residue containing one or more N atoms.

Among the compounds as above defined particularly preferred are those wherein:

n is as above defined;

R=H, $OR_2$ wherein $R_2$=H, methyl, ethyl, isopropyl, butyl, cyclopropyl, cyclopentyl, cyclohexyl, phenyl, benzyl;

$R_1$ is chosen in the group consisting of:

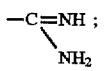

—$COOR_5$, wherein $R_5$ is chosen in the group consisting of H, methyl, ethyl, isopropyl, butyl, cyclopropyl, cyclopentyl, cyclohexyl, benzyl, phenyl or a residue of the cholesterol kind;

—B—$NR_6R_7$, wherein B is chosen in the group consisting of a simple chemical bond and the group C=O and wherein $R_6$ and $R_7$, independently from each other, are chosen in the group consisting of: H, methyl, ethyl, isopropyl, butyl, cyclopropyl, cyclopentyl, cycloesyl, benzyl, phenyl, or, taken together, $R_6$ and $R_7$ form a residue chosen in the group consisting of propylene, butylene, —$(CH_2)_2$—O—$(CH_2)_2$—, —$(CH_2)_2$—NH—$(CH_2)_2$—;

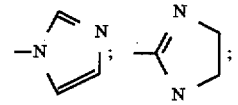

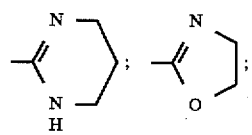

$R_3$ and $R_4$, independently from each other, are: H, methyl, ethyl, isopropyl, butyl, cyclopentyl, cyclopropyl, cyclohexyl or a benzyl group, phenyl, pyrrol, 1-methylpyrrol, thiophene, furan, thiazole, pyridine, imidazole, possibly substituted by a formamido or carbamoyl-group or, taken together, form a group propylene, butylene, —$(CH_2)_2$—O—$(CH_2)_2$—, —$(CH_2)$—NH—$(CH_2)_2$—;

A is a simple chemical bond or the group CO—NH—Z wherein Z is a methylene-, ethylene-, propylene-, p-phenylene-residue.

Pharmaceutically acceptable salts of compounds of formula (I) comprise the salts formed with pharmaceutically acceptable acids, either inorganic (as hydrochloric, hydrobromic, sulforic, nitric) or organic as acetic, propionic, succinic, malonic, citric, tartaric, methansulphonic, p-toluensulfonic and the like; also included are salts with pharmaceutically acceptable bases, either inorganic as sodium, potassium, calcium, magnesium, zinc, alluminium idroxides, or organic as amines like methylamine, diethylamine, trimethylamine or piperidine.

Particularly preferred are the compounds of formula (I) wherein:

1) n=2, R=$NH_2$, A=—$CONHCH_2CH_2$—, $R_1$=

hydrochloride 2) n=3, R=$NH_2$, A=—$CONHCH_2CH_2$—, $R_1$=

hydrochloride 3) n=4, R=$NH_2$, A=—$CONHCH_2CH_2$—, $R_1$=

hydrochloride 4) n=2, R=$NH_2$, A=—$CONHCH_2CH_2$—, $R_1$=$NH_2$, hydrochloride 5) n=3, R=$NH_2$, A=—$CONHCH_2CH_2$—, $R_1$=$NH_2$, hydrochloride 6) n=2, R=$NH_2$, A=—$CONHCH_2CH_2$—, $R_1$=$N(CH_3)_2$, hydrochloride 7) n=3, R=$NH_2$, A=—$CONHCH_2CH_2$—, $R_1$=$N(CH_3)_2$, hydrochloride 8) n=2, R=N(CH$_3$)$_2$, A=—CONHCH$_2$CH$_2$—, R$_1$=

hydrochloride 9) n=2, R=NH$_2$, A=—CONHCH$_2$CH$_2$—, R$_1$=COOH, sodium salt
10) n=3, R=NH$_2$, A=—CONHCH$_2$CH$_2$—, R$_1$=COOH sodium salt
11) n=2, R=NH$_2$, A=chemical bond, R$_1$=COOH sodium salt
12) n=3, R=NH$_2$, A=chemical bond, R$_1$=COOH sodium salt
13) n=2, R=OH, A=—CONHCH$_2$CH$_2$—, R$_1$=CONH$_2$ sodium salt
14) n=3, R=OH, A=chemical bond, R$_1$=CONH$_2$ sodium salt
15) n=2, R=OCH$_3$, A=—CONHCH$_2$CH$_2$—, R$_1$=

hydrochloride 16) n=2, R=NH$_2$, A=—CONHCH$_2$CH$_2$—, R$_1$=

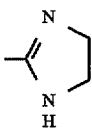

hydrochloride 17) n=2, R=NH$_2$, A=—CONHCH$_2$CH$_2$—, R$_1$=

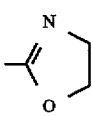

hydrochloride 18) n=2, R=NH$_2$, A=—CONHCH$_2$CH$_2$—, R$_1$=

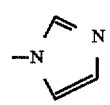

hydrochloride 19) n=2, R=

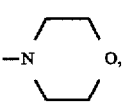

A=—CONHCH$_2$CH$_2$—, R$_1$=

, hydrochloride 20) n=2, R=NH$_2$, A=—CONHCH$_2$CH$_2$—, R$_1$=

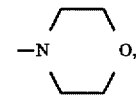

hydrochloride 21) n=2, R=NH$_2$, A=—CONHCH$_2$CH$_2$—, R$_1$=

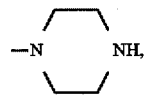

hydrochloride

The compounds of general formula (I) can be prepared according to the following processes.

a) Reductive lysis of compounds of formula (III)

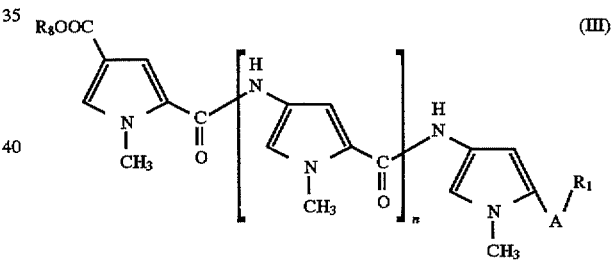

wherein n, A, R$_1$ are as above defined, excluded the case wherein R$_1$ is the group COOH or an N-containing heterocycle, and R$_8$ is a carboxylic acid protective group as for example 2,2,2-trichloroethyle, benzyle, phenylacyle.

The R$_8$ group remotion can be performed for example with Zn in acetic acid or by catalytic-hydrogenation on Pd/C in H$_2$O, MeOH, EtOH, HCOOH or mixtures thereof, to give compounds of formula (I) wherein n, A, R$_1$ are as defined, excluded the case wherein R$_1$=COOH or an N-containing heterocycle, and R=OH.

b) Reductive lysis or hydrogenation of compounds of formula (IV)

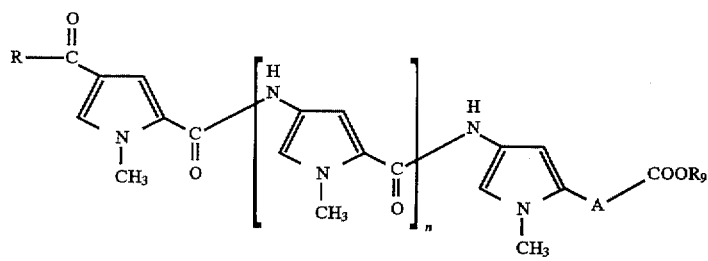

(IV)

wherein n and R are as above defined, excluded the case wherein R=OH, A is a simple chemical bond and R₉ is a carboxylic acid protective group as methyl, ethyl, t-butyl, benzyl. The group R₉ remotion can be performed according to known techniques as for example in T. W. Greene—Protective groups in Organic Synthesis—Wiley Interscience Publication 1981.

Operating as above said compounds of formula (I) are obtained wherein n and R are as above defined, R₁ is COOH, A is a simple chemical bond excluded the case wherein R=OH.

c) Hydrolysis of compounds of fomula (V)

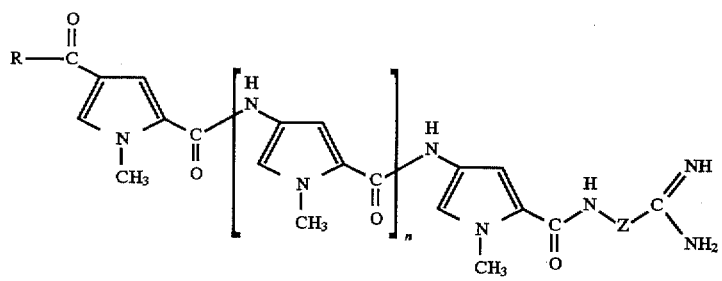

(V)

wherein n, R and Z are as above defined.

The hydrolisys can be performed under basic conditions, for example with NaOH in refluxing methanol, to give compounds of formula (I) wherein n and R are as above defined excluded the case wherein R=OH or OR₂, A=—CO—NH—CH₂—CH₂ and R₁=—COOH.

d) Compounds of formula (I) wherein n and R are as previously defined, A is the group CO—NH—Z— wherein Z is as defined and R₁ is an heterocycle-residue containing one or more N atoms can be obtained by conversion of compounds of formula (I) wherein n, R, Z are as hereabove defined and R₁=

The conversion of the group R₁ into an heterocyclic ring containing nitrogen, for example 2-imidazole, can be performed by reaction for example with an aminoacetaldehyde dimethyl acetal according to known procedures.

e) By reaction of a compound of formula (VI)

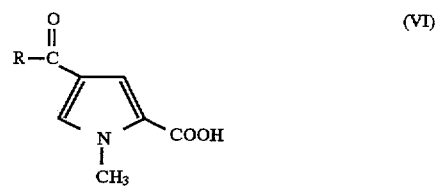

(VI)

wherein R is as above defined, excluded the case wherein R=OH, or an active derivative thereof, with a compound of formula (VII)

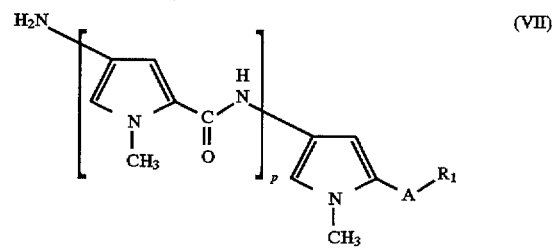

(VII)

wherein p=0–4, A and R₁ are as above defined excluded the case wherein R₁=COOH or an N-containing heterocycle.

The reaction between a compound of formula (VI) and a compound of formula VII is performed in the presence of condensing agents like DCC (dicycloesylcarbodiimide) or EDC ([1-(3-dimethylaminopropyl)-3-ethylcarbodiimide hydrochloride] and in the presence or absence of hydroxybenzotriazole or BOP (benzotriazol-1-yloxytris (dimethylaminophosphoniumesafluorophosphate) or using an active derivative of VI as for example the corresponding acylchloride, acylimidazole, acylazide of the acid VI or an active ester, as for example the 2,4,5-trichlorophenoxyester or N-oxysuccinimidoester, of acid VI or of the anhydride thereof.

Preferably, the reaction between VI and VII is performed using molar ratios comprised between 1:1 and 1:3 in an organic solvent as dimethylsolfoxide, esamethylphosphorotriamide, dimethylacetamide, or preferably dimethylformamide in the presence of a condensing agent of the kind specified above and of N-hydroxybenzotriazole or BOP and in the presence of an organic base as triethylamine, diisopropylethylamine and 1,8-bis-(dimethylamino)-naphtaline.

The reaction temperature is comprised between –10° C. and 50° C. the reaction time is 2–48 hours.

If preferred, the reaction between a compound of formula (V) and a compound of formula (VII) can be performed using a reactive derivative of a compound of fomula (VI) as previously described and thereafter performing the reaction in a bi-phasic system water-organic solvent as for the amidation according to Schotten-Baumann or in an organic solvent possibly in the presence of an inorganic or organic base. The reaction usually takes place at room temperature and the required reaction time is 2–24 hours.

The compound of formula (III) as indicated in process (a) can be prepared by reaction of a compound of formula (VIII)

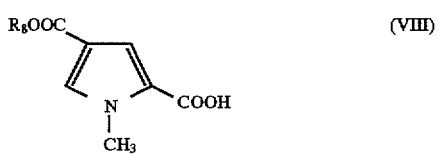

wherein $R_8$ is as above defined, or an active derivative thereof, and a compound of formula (VII) wherein p, A, $R_1$ are as above defined. p The reaction can be performed under the same conditions described for the amidation reaction between the compound of formula VI with a compound of formula (VII).

The compounds of formula (VIII) can he prepared as described in the Italian application No. 22154 in the name of the applicant and herein reported as reference.

The compound of formula (IV) used in process (b) can be prepared by reaction of a compound of formula VI wherein R is as above defined, excluded the case wherein R=OH, or an active derivative thereof, with a compound of formula (IX)

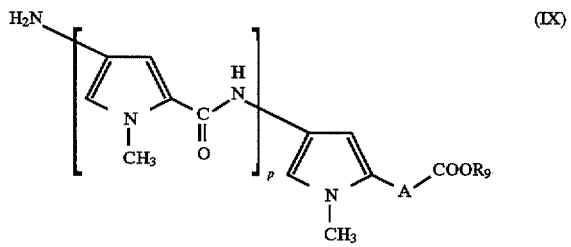

wherein p is 0 or is comprised between 1 and 4 and $R_9$ is as above defined.

The reaction between compounds VI and IX is similar to the one described for the compounds VI and VII.

The compound of formula (VI) wherein R=H, used in process (e), can be prepared as described in J.O.C. 43, 4849 (1978).

The compounds of formula (VI) wherein R=$OR_2$, wherein $R_2$ is as above defined excluded the case wherein $R_2$=OH, can be prepared according to the methods and procedures already described for the compounds of formula (VIII).

The compounds of formula (VI) wherein R=$NR_3R_4$ wherein $R_3$ and $R_4$ are as above defined can be prepared according to the known methods and procedures for the amidation of pyrrol-dicarboxylic acids as reported in the International application No. WO 93/13739.

Compounds of formula (IX), wherein p, $R_9$ and A are as above defined in the case of process (b), and compounds of formula VII wherein p is as defined, A is a simple chemical, bond $R_1$ is $COOR_5$ wherein $R_5$ is as above defined, excluded the case wherein $R_5$=H, can be prepared according to known methods and procedures. Compounds of formula (VII) as described in process (e) wherein p is as above defined, A is the group CO—NH—Z and $R_1$ is as above defined can be prepared through the reaction of acid (X)

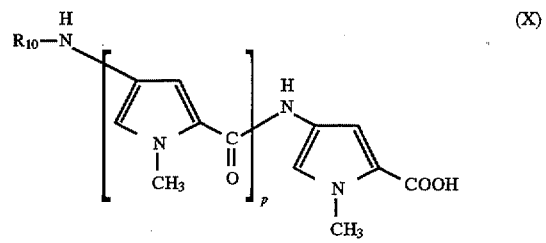

wherein p is 0 or an integer comprised between 1 and 4 and $R_{10}$ is an protective group for the amino-group as for example formyl, trifluoroacetyl, t-butyle-oxycarbonyl and the like, with the aminoacid (XI)

$$H_2N-Z-COOR_5 \quad (XI)$$

wherein $R_5$ is as above defined followed by the remotion of the group $R_{10}$.

The reaction between the compounds X and XI is similar to the one descrobed for compounds VI and VII.

The compounds of formula (IX) are known or can be prepared with known procedures as for example described in J.O.C. 46, 3492 (1981).

The remotion of protective group $R_{10}$ can be performed according to known methods and procedures.

The compounds of formula (VII) wherein p and A are as defined in process (e) and $R_1$ is the group —B—$NR_6R_7$, wherein B is as above defined, or the group

are known or can be prepared through known procedure.

The compounds of the present invention are useful as antiparasitic and antiviral agents.

In particular they show a specific anti-malaric activity by strongly inhibiting the proliferation of Plasmodium Falciparum strains, either resistent or not to the commonly used pharmaceuticals as chloroquine.

Moreover the compounds proved effective in interferring with the reproductive activity of the patogenous virus.

The compounds of the invention can be administered orally or parenterally for example by injection or infusion intravenously or intramuscularly.

The dosage is dependent from the age, weight and general conditions of the patient and from the administration way, for example an effective dosage for an adult can be comprised between about 0.1 and about 100 mg pro dose administered from 1 to 4 times per day.

The present invention refers also to the pharmaceutical compositions comprising as active principle a compound of general formula (I) as previously defined or a pharmaceutically acceptable salt thereof in combination with a pharmaceutically acceptable carrier or diluent.

For example the solutions for infusion or intravenuous injection can contain sterile water or a salt isotonic solution as carrier.

The solutions or suspensions for intramuscular injections can contain as carrier for example sterile water, glycols as propylene glycol, olive oil, ethyl oleate.

Solid oral forms can contain as diluent, for example, saccharose, lactose, cellulose, mais starch; as lubrificants silica, talc, calcium or magnesium stearate, polyethylen glycols, binders (as starchs, methylcellulose, polyvinyl pyrrolidone, arabic gum) disaggregants as alginates, alginic acid or amides, watering substances like polysorbates, laurylsulfates or lecitine, dyes, sweeteners.

Example 1

3-[1-Methyl-4-[1-methyl-4-[1-methyl-4-[1-methyl-4-(carboxyamido)pyrrol -2-carboxyamido]pyrrol-2-carboxyamido]pyrrol-2-carboxyamido]pyrrol-2-carboxyamido] propionamidine hydrochloride (Compound of formula (I) wherein: n=2, R=NH$_2$, A=CONHCH$_2$CH$_2$, R$_1$

A mixture of 1-methyl-4-carboxyamidopyrrol-2-carboxylic acid (816 mg, 4.88 mmoles) and carbonyldiimidazole (800 mg, 4.9 mmoles) in anhydrous DMF (100 ml) is stirred at 40° C. for 2 hours.

After cooling to room temperature the reaction mixture is added with a solution of N-deformyldystamicine (2 g, 3.8 mmoles) in anhydrous DMF (5 ml). After 2 hours stirring at 40° C. the reaction mixture is evaporated to dryness and the residue is separated by silica gel chromatography (eluent CHCl$_3$/MeOH 7/3) giving 1.89 g of the wanted product (yield 78%).

$^1$H-NMR (DMSOd$_6$), δ:2.61 (t,2H), 3.49 (m, 2H), 3.80 (s, 3H), 3.84 (s, 3H), 3.85 (s, 3H), 3.87 (s, 3H), 6.83 (bs, 1H), 6.94 (d, 1H), 7.04 (d, 1H), 7.05 (d, 1H), 7.17 (d, 1H), 7.23 (d, 2H), 7.26 (d, 1H), 7.38 (bs, 1H), 7.49 (d, 1H), 8.21 (t, 1H), 8.64 (bs, 2H), 8.97 (bs, 2H), 9.90 (s, 1H), 9.95 (s, 1H), 10.1 (s, 1H).

Following the same procedure the following compound of formula (I) was obtained:

3-[1-Methyl-4-[1-methyl-4-[1-methyl-4-[1-methyl-4-(carboxyamido)pyrrol-2-carboxyamido]pyrrol-2-carboxyamido]pyrrol-2-carboxyamido]pyrrol-2-carboxyamido]pyrrol-2-carboxyamido] propionamidine hydrochloride (Compound of formula (I) wherein: n=3, R=NH$_2$, A=CONHCH$_2$CH$_2$, R$_1$

$^1$H-NMR (DMSOd$_6$), δ:2.61 (t,2H), 3.51 (m, 2H), 3.82 (s, 3H), 3.85 (s, 3H), 3.87 (s, 6H), 3.88 (s, 3H), 6.85 (bs, 1H), 6.96 (d, 1H), 7.06 (d, 1H), 7.08 (d, 2H), 7.19 (d, 1H), 7.25 (d, 3H), 7.28 (d, 1H), 7.39 (bs, 1H), 7.51 (bs, 1H), 8.22 (t, 1H), 8.63 (bs, 2H), 8.98 (bs, 2H), 9.92 (s, 1H), 9.95 (s, 1H), 9.97 (s, 1H), 10.8 (s, 1H).

We claim:

1. Compounds of general formula (I)

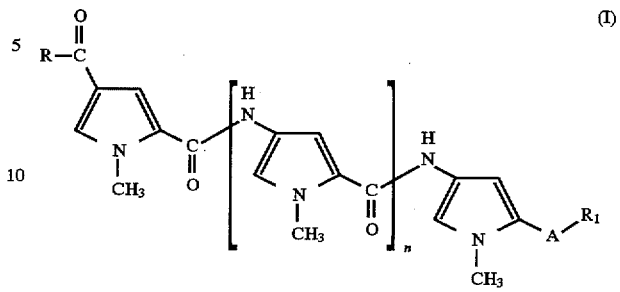

and pharmaceutically acceptable salts thereof wherein:

n is 0 or an integer comprised between 1 and 4;

R is selected from the group consisting of H, —OR$_2$, or —NR$_3$R$_4$ wherein:

R$_2$ is selected from the group consisting of H, methyl, ethyl, isopropyl, butyl, cyclopropyl, cyclopentyl, cyclohexyl, phenyl or benzyl;

R$_3$ and R$_4$, independently from each other, are selected from the group consisting of H, methyl, ethyl, isopropyl, butyl, cyclopentyl, cyclopropyl, cyclohexyl or a benzyl group, phenyl, pyrrol, 1-methylpyrrol, thiophene, furan, thiazole, pyridine or imidazole, optionally substituted by a formamido or carbamoyl-group or, when taken together, from a group selected from propylene, butylene, —(CH$_2$)$_2$—O—(CH$_2$)$_2$— or —(CH$_2$)—NH—(CH$_2$)$_2$—;

R$_1$ is selected from the group consisting of:

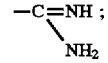

—COOR$_5$, wherein R$_5$ is selected from the group consisting of H, methyl, ethyl, isopropyl, butyl, cyclopropyl, cyclopentyl, cyclohexyl, benzyl, phenyl or a cholesterol type group;

—B—NR$_6$R$_7$ wherein B is selected from the group consisting of a simple chemical bond and the group C=O and wherein R$_6$ and R$_7$, independently from each other, are selected from the group consisting of H, methyl, ethyl, isopropyl, butyl, cyclopropyl, cyclopentyl, cyclohexyl, benzyl or phenyl, or, taken together, form a group selected from propylene, butylene, —(CH$_2$)$_2$—O—(CH$_2$)$_2$— or —(CH$_2$)$_2$—NH—(CH$_2$)$_2$—;

a heterocyclic group selected from

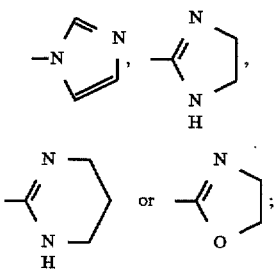

A is a simple chemical bond or the group CO—NH—Z wherein Z is a methylene-, ethylene-, propylene- or p-phenylene group with the proviso that:

when $R_1$ is —B—$NR_6R_7$ and B is a simple chemical bond, A is not a simple chemical bond;

when $R_1$ is one of the above indicated heterocyclic groups, A is not a simple chemical bond;

when R is $NH_2$, A is the group CO—NH—Z, wherein Z is —$CH_2$—$CH_2$ and $R_1$ is

then n is different from 1;

when R is the group $NH_2$, $R_1$ is —COOH and A is a simple chemical bond, then n is different from 0;

when R is OH, $R_1$ is

and A is the group —CO—NH—Z, then Z is different from —$CH_2$—$CH_2$.

2. Compounds of formula (I) according to claim 1 wherein:

1) n=2, R=$NH_2$, A=—$CONHCH_2CH_2$—, $R_1$=

hydrochloride 2) n=3, R=$NH_2$, A=—$CONHCH_2CH_2$—, $R_1$=

hydrochloride 3) n=4, R=$NH_2$, A=—$CONHCH_2CH_2$—, $R_1$=

hydrochloride 4) n=2, R=$NH_2$, A=—$CONHCH_2CH_2$—, $R_1$=$NH_2$, hydrochloride
5) n=3, R=$NH_2$, A=—$CONHCH_2CH_2$—, $R_1$=$NH_2$, hydrochloride
6) n=2, R=$NH_2$, A=—$CONHCH_2CH_2$, $R_1$=$N(CH_3)_2$, hydrochloride
7) n=3, R=$NH_2$, A=—$CONHCH_2CH_2$—, $R_1$=$N(CH_3)_2$, hydrochloride
8) n=2, R=$N(CH_3)_2$, A=—$CONHCH_2CH_2$—, $R_1$=

hydrochloride 9) n=2, R=$NH_2$, A=—$CONHCH_2CH_2$—, $R_1$=COOH sodium salt
10) n=3, R=$NH_2$, A=—$CONHCH_2CH_2$—, $R_1$=COOH sodium salt
11) n=2, R=$NH_2$, A=chemical bond, $R_1$=COOH sodium salt
12) n=3, R=$NH_2$, A=chemical bond, $R_1$=COOH sodium salt
13) n=2, R=OH, A=—$CONHCH_2CH_2$—, $R_1$=$CONH_2$ sodium salt
14) n=3, R=OH, A=chemical bond, $R_1$=$CONH_2$ sodium salt
15) n=2, R=$OCH_3$, A=—$CONHCH_2CH_2$—, $R_1$=

hydrochloride 16) n=2, R=$NH_2$, A=—$CONHCH_2CH_2$—, $R_1$=

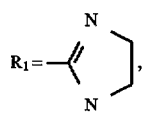

hydrochloride 17) n=2; R=$NH_2$, A=—$CONHCH_2CH_2$—, $R_1$=

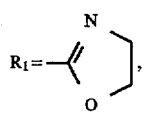

hydrochloride 18) n=2, R=$NH_2$, A=—$CONHCH_2CH_2$—, $R_1$=

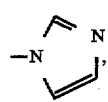

hydrochloride 19) n=2, R=

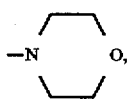

A=—$CONHCH_2CH_2$—, $R_1$=

=C=NH,
   \
    $NH_2$ hydrochloride 20) n=2, R=$NH_2$, A=—$CONHCH_2CH_2$—, $R_1$=

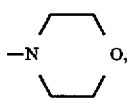

hydrochloride and 21) n=2, R=NH$_2$, A=—CONHCH$_2$CH$_2$—, R$_1$=

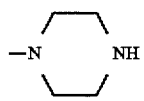

hydrochloride.

3. Pharmaceutical compositions comprising as active principle a compound according to claim 1 in combination with pharmaceutically acceptable diluent or carrier.

4. Pharmaceutical compositions according to claim 3, as antiparasitic agents.

5. Pharmaceutical compositions according to claim 4, wherein the parasitic agents are: plasmodia, trypanosomes, protozoa of the genus Leishmania, *Toxoplasma gondii*, *Pneumocystis carinii* and *Criptosporidum parvum*.

6. Pharmaceutical compositions according to claim 4 as anti-malaric agents.

7. Method for the prophylaxis and therapeutic treatment of malaria and diseases caused by Leishmania, *Toxoplasma gondii*, *Pneumocystis carinii* and *Criptosporidum parvum* wherein pharmaceutical compositions, containing as active principle a compound according to claim 1 in combination with a pharmaceutically acceptable carrier or diluent, are administered to the patient, 1 to 4 times per day, in a quantity comprised between 0.1 and 100 mg pro dose of active principle.

* * * * *